US00PP32985P2

(12) United States Plant Patent
Neessen et al.

(10) Patent No.: US PP32,985 P2
(45) Date of Patent: Apr. 20, 2021

(54) ***CERCIS* TREE NAMED 'SEIRB'**

(50) Latin Name: *Cercis canadensis*
Varietal Denomination: SEIRB

(71) Applicants: Suzanne Neessen, Marshall, VA (US); Elaine Chrisman, Marshall, VA (US)

(72) Inventors: Suzanne Neessen, Marshall, VA (US); Elaine Chrisman, Marshall, VA (US)

( * ) Notice: Subject to any disclaimer, the term of this patent is extended or adjusted under 35 U.S.C. 154(b) by 0 days.

(21) Appl. No.: 16/873,807

(22) Filed: Jul. 13, 2020

(51) Int. Cl.
*A01H 6/54* (2018.01)
*A01H 5/00* (2018.01)

(52) U.S. Cl.
USPC ..... Plt./216

(58) Field of Classification Search
USPC ..... Plt./216
CPC ..... A01H 6/54; A01H 5/00
See application file for complete search history.

*Primary Examiner* — Keith O. Robinson
(74) *Attorney, Agent, or Firm* — Penny J. Aguirre

(57) ABSTRACT

A new cultivar of *Cercis canadensis* tree named 'SEIRB' that is characterized by its stems that form a "zig-zag" growth pattern, its semi-weeping plant habit, its flowers that are deep pink in color and its dense plant form.

2 Drawing Sheets

Botanical classification: *Cercis canadensis.*
Variety denomination: 'SEIRB'.

BACKGROUND OF THE INVENTION

The present invention relates to a new and distinct cultivar of *Cercis canadensis* and will be referred to hereafter by its cultivar name, 'SEIRB'. 'SEIRB' is an Eastern redbud tree grown for use as a landscape plant.

The new *Cercis* was discovered by one of the Inventors in April of 2012 in a cultivated field in Marshall, Va. The parentage is unknown.

Asexual propagation of the new cultivar was first accomplished by side veneer grafting under the direction of the Inventors in summer of 2015 in Belvidere, Tenn. Asexual propagation by side veneer grafting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'SEIRB' as a unique cultivar of *Cercis.*

1. 'SEIRB' exhibits stems that form a "zig-zag" growth pattern.
2. 'SEIRB' exhibits a semi-weeping plant habit.
3. 'SEIRB' exhibits flowers that are deep pink in color.
4. 'SEIRB' exhibits a dense plant form.

'SEIRB' can be compared to the *Cercis canadensis* cultivars 'Ruby Falls' (U.S. Plant Pat. No. 22,097), and 'Merlot' (U.S. Plant Pat. No. 22,297). 'Ruby Falls' differs from 'SEIRB' in having a stronger weeping plant habit, stems that are straight with no zig zag pattern, flowers that are more purple in color and foliage that is purple in color in the spring turning to a dark burgundy color as the plant matures. 'Merlot' differs from 'SEIRB' in having a more upright plant habit, stems that are straight with no zig zag pattern, flowers that are lavender in color, and very glossy foliage that emerges purple, changes to darker burgundy and then green as it matures.

BRIEF DESCRIPTION OF THE DRAWINGS

The accompanying colored photographs illustrate the overall appearance and distinct characteristics of the new *Cercis*. The photographs were taken of a tree approximately 20-years in age as the original discovered tree in Marshall, Va.

The photograph in FIG. 1 provides a view of the plant habit of 'SEIRB' in bloom.

Figure 1:
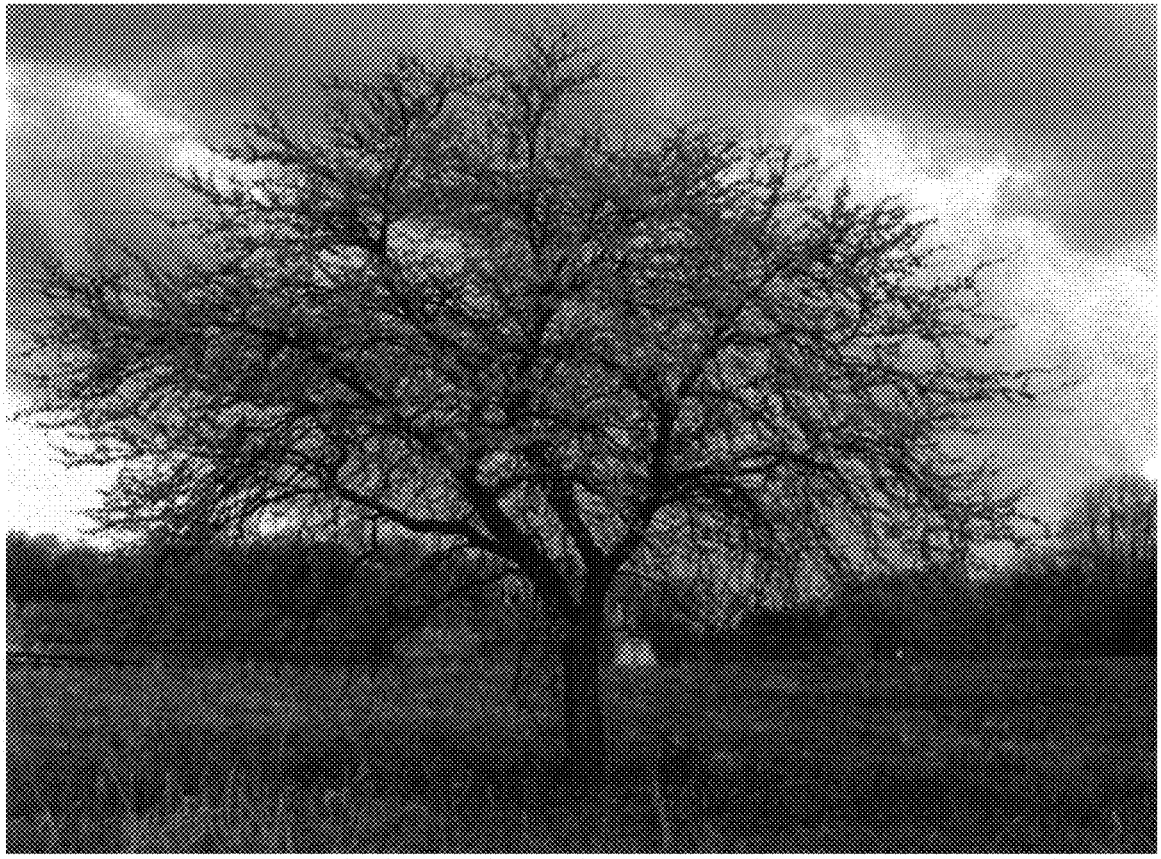
Figure 2:
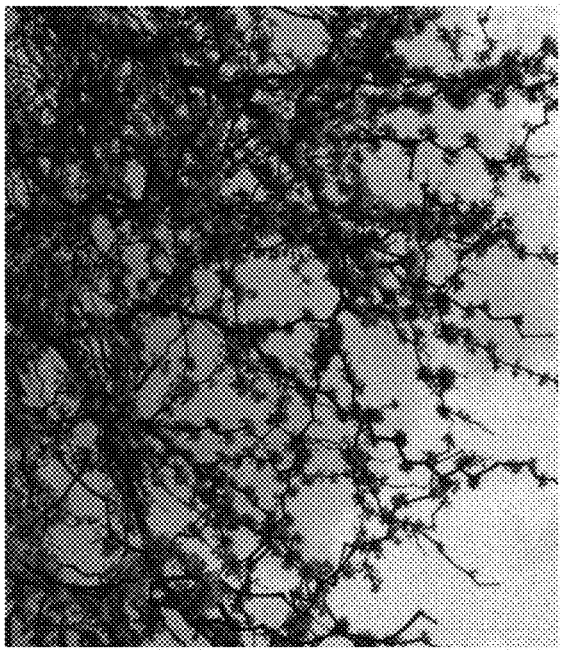

The photograph in FIG. 2 provides a view of the zig-zag branches in bloom of 'SEIRB'.

Figure 3:
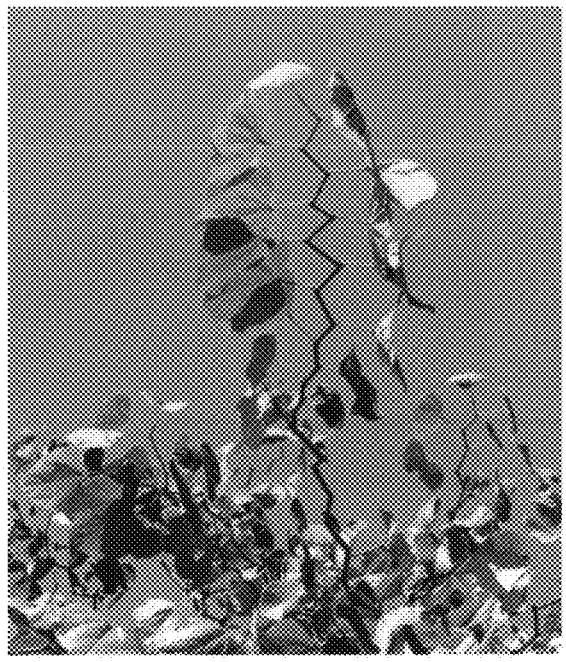

The photograph in FIG. 3 provides a view of the zig-zag branches of 'SEIRB' with foliage.

Figure 4:
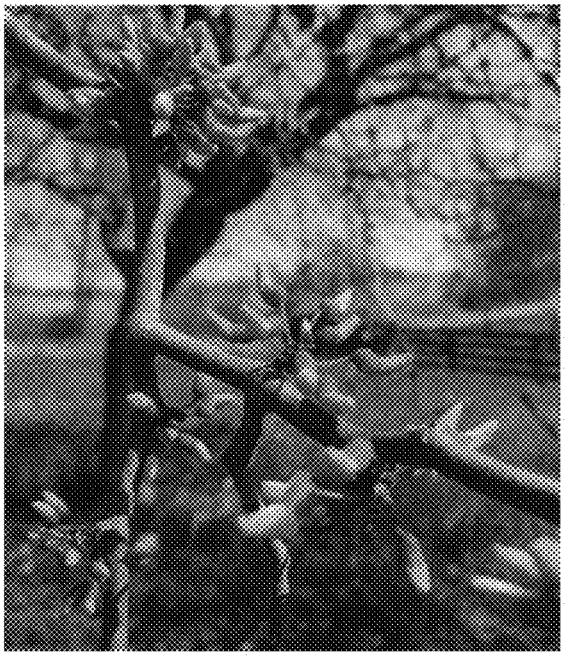

The photograph in FIG. 4 provides a close-up view of the flowers of 'SEIRB'.

The colors in the photographs are as close as possible with the digital photography techniques available, the color values cited in the detailed botanical description accurately describe the colors of the new *Cercis.*

DETAILED BOTANICAL DESCRIPTION

The following is a detailed description of a 3-year-old plants of the new cultivar as grown in a 5-gallon container in Belvidere, Tenn. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—2 to 3 weeks in April in Virginia.
*Plant type.*—Deciduous tree.
*Plant habit.*—Semi-weeping and densely branched.

*Height and spread*.—Reaches about 118 cm in height and 75 cm in spread as grown in a container as a 3-year-old plant and reaches 6 m in height and 8.5 m in width as a mature plant in the landscape.

*Cold hardiness*.—At least to U.S.D.A. Zone 5.

*Diseases and pests*.—No susceptibility or resistance to diseases or pests has been observed.

*Root description*.—Fibrous, 199A and N200B in color.

*Propagation*.—Veneer grafting.

*Propagation timing*.—Grafting in July-August, growth begins in the spring and takes 7 months to become a salable whip.

*Growth rate*.—Moderate.

Branch description:

*Branch shape*.—Rounded, zig-zag growth habit with numerous bends back and forth throughout the stems.

*Branch color*.—New growth, ranging between 143A, N144B, N144C, 200A and N186A, mature branches; a blend of 200A and N200B and very densely covered with lenticels 199B in color, mature bark; 199C and N200B and very densely covered with lenticels 156C in color.

*Branch size*.—Main trunk; an average of 3 cm in width and 41 cm in length (until lateral branching), lateral branches; an average of 49 cm in length and 2 cm in width, new growth; an average of 2.5 mm in width.

*Branch surface*.—Young branches; glabrous, semi-glossy, mature bark; glabrous, matte luster, relatively smooth, and very heavily lenticellate.

*Internode length*.—An average of 4 cm.

*Branching habit*.—An average of 5 lateral branches.

Foliage description:

*Leaf shape*.—Reniform.

*Leaf division*.—Simple.

*Leaf base*.—Cordate to truncate.

*Leaf apex*.—Obcordate, sometimes multi-lobed, lobes moderately deep about 5 mm in depth.

*Leaf fragrance*.—None.

*Leaf venation*.—Palmate, color; young upper and lower surface N144D and 145C, mature leaves upper and lower surface 144B.

*Leaf margins*.—Entire.

*Leaf arrangement*.—Alternate in a zig zag formation.

*Leaf aspect*.—Held reflexed downward from petiole (hanging) to outward.

*Leaf attachment*.—Petiolate.

*Leave number*.—An average of 18 leaves per a stem 30 cm in length.

*Leaf surface*.—New and mature leaf upper surface; smooth, glabrous, satiny and shiny, new and mature leaf lower surface; smooth, glabrous, satiny and dull.

*Leaf size*.—An average of 4 cm in length and 6 cm in width.

*Leaf color*.—Emerging leaf upper and lower surface; N34A to 144A, young leaf upper and lower surface; N144C to 144A, mature leaf upper and lower surface; 143A to 144A.

*Petiole*.—An average of 4.5 cm in length and 1 mm in width, glabrous surface, flexible and moderately strong, color; young 144A, mature 144A and 154A.

*Internode length*.—Ranging between 1 cm and 2 cm.

Inflorescence description:

*Inflorescence type*.—Cauliflorous clusters of papilionaceous (pea-like) flowers.

*Inflorescence size*.—Up to 3 cm in width and 3.5 cm in depth.

*Lastingness of inflorescence*.—2 to 3 weeks.

*Flower size*.—An average of 1.5 cm in length and 1 cm in width.

*Flower fragrance*.—Faint.

*Flower number*.—An average of 10 flowers per cluster.

*Bracts*.—About 5 per inflorescence, imbricate, ovate in shape, an average of 1.5 mm in length and 1 mm in width, color; 200A, glabrous surface, matte luster.

*Peduncles*.—An average of 2 cm in length and less than 0.5 mm in width, color; N75A at the top closest to the flower, 70A towards the base, glabrous surface, matte luster, weak strength, floppy, held at all directions from branch node.

*Pedicels*.—None, peduncles attached in cluster at branch.

*Flower buds*.—Slightly curved, cone-shaped, about 10 mm in length and 2 mm in width, color; 72A, N75A at the base, calyx 71A, glabrous surface, matte luster.

*Flower type*.—Papilionaceous.

*Calyx*.—Campanulate in shape, comprised of 5 fused sepals; an average of 5 mm in length, entire margins, color N78, base N79A, glabrous surface, matte luster.

*Corolla features*.—Papilionaceous, bilateral with two outer petals, a center petal, and an inner labium folded around the stamens and pistil, outer and central petals; obovate to rotund in shape, curled edges, average of 1 cm in length and 3 mm in width, center petal 8 mm in length and 2.5 mm in width, rounded apex, cuneate base, entire margins to slightly wavy and curled, color; a blend between 91B, N82D, N78A, margins and base 92D, inner labium; ovate in shape, about 1.2 cm in length and 4 mm in width, rounded apex, cuneate base, entire margins are cupped inward and lightly wavy, color; N78A, base N78D, inner and outer surfaces glabrous, matte luster.

Reproductive organs:

*Gynoecium*.—Pistil; 1, stigma; minute and oval in shape, an average of under 0.5 mm in length and width, 158A in color, style; an average of 1 cm in length and 1 mm in width, color; 162A, changing to 186C at the top, ovary; superior and inserted obliquely at bottom of calyx and 155B in color.

*Androecium*.—Stamens; 10 anthers; club-shaped to oval in shape, an average of 0.75 mm in length and less than 0.5 mm in width, 200A in color, filament; an average of 9 mm in length and 0.5 mm in width, colors range between 73A, 63B and 71B, glossy surface cluster, pollen is moderate in quantity and 10A in color.

*Sterility*.—Self-incompatible.

*Seed*.—None observed.

It is claimed:

1. A new and distinct cultivar of *Cercis canadensis* tree named 'SEIRB' as herein illustrated and described.

* * * * *